(12) United States Patent
Carter et al.

(10) Patent No.: US 10,473,584 B2
(45) Date of Patent: Nov. 12, 2019

(54) DIFFUSE REFLECTANCE INFRARED FOURIER TRANSFORM SPECTROSCOPY

(71) Applicant: PerkinElmer Singapore PTE Ltd., Singapore (SG)

(72) Inventors: Ralph Lance Carter, Thame (GB); Robert Alan Hoult, Beaconsfield (GB)

(73) Assignee: PerkinElmer Singapore PTE Limited, Singapore (SG)

( * ) Notice: Subject to any disclaimer, the term of this patent is extended or adjusted under 35 U.S.C. 154(b) by 0 days.

(21) Appl. No.: 15/985,032

(22) Filed: May 21, 2018

(65) Prior Publication Data

US 2018/0266942 A1 Sep. 20, 2018

Related U.S. Application Data

(63) Continuation of application No. 14/905,685, filed as application No. PCT/GB2014/000286 on Jul. 14, 2014, now Pat. No. 9,976,949.

(51) Int. Cl.
*G01N 21/35* (2014.01)
*G01J 3/08* (2006.01)
(Continued)

(52) U.S. Cl.
CPC .............. *G01N 21/35* (2013.01); *G01J 3/021* (2013.01); *G01J 3/0262* (2013.01);
(Continued)

(58) Field of Classification Search
CPC .............. G01N 21/35; G01N 21/4738; G01N 2021/3595; G01N 2201/061;
(Continued)

(56) References Cited

U.S. PATENT DOCUMENTS 5,327,219 A 7/1994 Steimle et al.
5,473,438 A 12/1995 Keranen et al.
(Continued)

FOREIGN PATENT DOCUMENTS

JP S6014132 A 1/1994
WO 197900464 A 7/1979

OTHER PUBLICATIONS

"Diffuse Reflectance Measurements by Infrared Fourier Transform Spectrometry", Analytical Chemistry, vol. 50, No. 13, p. 1906-1910, Nov. 1978 by Fuller et al.*
(Continued)

*Primary Examiner* — Jamil Ahmed
(74) *Attorney, Agent, or Firm* — Lando & Anastasi, LLP (57) ABSTRACT

Diffuse reflectance spectroscopy apparatus for use in analyzing a sample comprising a sample receiving location 2 for receiving a sample 3 for analysis; an illumination arrangement 4 for directing light towards a received sample; a detector 6 for detecting light reflected by a received sample; and collection optics 5 for directing light reflected by a received sample towards the detector. The illumination arrangement further comprises an interferometer 42 and a half beam block 45a, 45b which is disposed substantially at a focus in the optical path for blocking light which exits the interferometer, passes said focus, and is reflected from re-entering the interferometer. A half beam block 45a may be disposed in the optical path between the interferometer and the light source 41 for blocking light that exits the interferometer back towards the light source and is reflected by the light source from re-entering the interferometer and/or a half beam block 45b may be disposed in the optical path on the opposite side of the interferometer than the light source.

32 Claims, 6 Drawing Sheets

(51) Int. Cl.
*G01J 3/02* (2006.01)
*G01J 3/453* (2006.01)
*G01N 21/47* (2006.01)

(52) U.S. Cl.
CPC ........... *G01J 3/0291* (2013.01); *G01J 3/0297* (2013.01); *G01J 3/08* (2013.01); *G01J 3/453* (2013.01); *G01N 21/4738* (2013.01); *G01J 2003/4534* (2013.01); *G01N 2021/3595* (2013.01); *G01N 2201/061* (2013.01); *G01N 2201/068* (2013.01)

(58) Field of Classification Search
CPC .. G01N 2201/068; G01J 3/021; G01J 3/0262; G01J 3/0291; G01J 3/0297; G01J 3/08; G01J 3/453; G01J 2003/4534
See application file for complete search history.

(56) References Cited

U.S. PATENT DOCUMENTS

| | | |
|---|---|---|
| 2002/0089667 A1 | 7/2002 | Kellerhals |
| 2006/0033911 A1 | 2/2006 | Brown et al. |
| 2010/0321686 A1 | 12/2010 | Correns et al. |
| 2013/0276507 A1* | 10/2013 | Andraos ................ G01D 18/00 73/1.03 |
| 2013/0278607 A1 | 10/2013 | Twigg et al. |

OTHER PUBLICATIONS

"Testing the radiometric accuracy of Fourier transform infrared transmittance measurements", Applied Optics, vol. 36, No. 34, p. 8896-8908, Dec. 1997 by Kaplan et al.*
Fuller et al., "Diffuse Reflectance Measurements by Infared Fourier Transform Spectrometry", Analytical Chemistry, vol. 50, No. 13, p. 1906-1910, Nov. 1978.
PerkinElmer Instruction Manual for Near Infared Reflectance Accessory.
Kaplan et al., "Testing the Radiometric Accuracy of Fourier Transform Infrared Transmittance Measurements", Applied Optics, vol. 36, No. 34, p. 8896, Dec. 1997.
Hirschfeld, T., "Multiple Order Spectra in Fourier Transform Infrared Spectroscopy", Applied Optics, vol. 16, No. 7, p. 1905, Jul. 1977.
Jackson, R.S., "Continuous Scanning Interferometers for Mid-infrared Spectrometry", Handbook of Vibrational Spectroscopy, vol. 1, p. 264-282, Aug. 2006.
Johnson et al., "Removing Aperture-Induced Artifacts from Fourier Transform Infrared Intensity Values", Applied Optics, vol. 41, No. 15, p. 2831, May 2002.
Wiley, R.R., "Fourier Transform Infrared Spectrophotometer for Transmittance and Diffuse Reflectance Measurements", Applied Spectroscopy, vol. 30, No. 6, p. 593-601, Jan. 1976.
Birch et al., an abstract of "Interreflection Errors in Fourier Transform Spectroscopy: A Preliminary Appraisal", vol. 380, No. 2-3, p. 369-378, Feb. 1999.

* cited by examiner

DIFFUSE REFLECTANCE INFRARED FOURIER TRANSFORM SPECTROSCOPY

CROSS-REFERENCE TO RELATED APPLICATIONS

This application is a continuation of U.S. patent application Ser. No. 14/905,685, titled DIFFUSE REFLECTANCE INFRARED FOURIER TRANSFORM SPECTROSCOPY and filed on Jan. 15, 2016, which is a U.S. national phase application and claims the benefit of priority under 35 U.S.C. § 371 of PCT/GB2014/000286, titled DIFFUSE REFLECTANCE INFRARED FOURIER TRANSFORM SPECTROSCOPY and filed on Jul. 14, 2014, which in turn claims priority to GB1312911.9, filed on Jul. 18, 2013, the contents of each of which are hereby incorporated herein by reference in their entireties for all purposes.

This invention relates to diffuse reflectance spectroscopy and in particular FT-IR (Fourier Transform Infra Red) diffuse reflectance spectroscopy apparatus and methods for manufacturing FT-IR diffuse reflectance spectroscopy apparatus.

In the field of reflectance spectroscopy a light beam is shone onto a sample. A portion of the light reflected from the sample is collected and subjected to spectroscopic analysis in order to determine the chemical composition of the sample.

Prediction of the chemical composition of the sample involves the use of statistical techniques (known as chemometrics) that relate the optical energies detected at various wavelengths to the concentration of a particular chemical species of interest.

In order to make such predictions, a calibration or model must first be built using standards of known concentration. The process of building such a model involves the use of many standards, each of which require analysis by some other (often wet chemistry) techniques. The alternative analysis methods are usually cumbersome and time consuming and thus expensive. Further, the standards that have been qualified often have a limited shelf life.

It is highly desirable that a calibration set built using one instrument can be transferred to another and be effective on a second instrument. It is often the case that small and subtle differences in response between notionally identical instruments cause a second instrument to read somewhat differently to a first when used to analyse the same sample. The best measurement accuracy is achieved by calibration of each instrument. However such a practice is often prohibitively expensive.

The more similar in response the instruments can be made, the more consistent are the predictions of sample properties.

It would be desirable to provide diffuse reflectance spectroscopy apparatus which are aimed at helping to reduce such variability and more generally to help improve performance.

Some particular considerations, taken into account when developing the presently described apparatus, included:

A tendency for the spectra measured by an apparatus to be dependent on the positioning of the sample relative to a source of illumination and/or detection system;

The tendency for differences in illumination between devices and at different times to affect the spectra obtained;

Errors which can be introduced by double modulation artefacts in FTIR spectroscopy;

The fact that there may be differences in background spectra from time to time and/or possible drifts or malfunctions in operation of the apparatus as a whole.

Various different features of the presently developed and described apparatus may help in addressing one or more of these issues.

According to a first aspect of the present invention there is provided diffuse reflectance spectroscopy apparatus for use in analysing a sample comprising:

a sample receiving location for receiving a sample for analysis;

an illumination arrangement for directing light towards a received sample;

a detector for detecting light reflected by a received sample; and collection optics for directing light reflected by a received sample towards the detector.

According to a second aspect of the present invention there is provided diffuse reflectance spectroscopy apparatus for use in analysing a sample comprising:

a sample receiving location for receiving a sample for analysis;

an illumination arrangement for directing light towards a received sample;

a detector for detecting light reflected by a received sample and having a predetermined light detecting active area; and collection optics for directing towards the detector, light reflected at an angle within a predetermined angular range by a received sample, wherein the collection optics focus the detector substantially at infinity.

This helps to avoid variations in the intensity and/or spectrum of light seen by the detector when the sample height (spacing between the sample and collection optics) varies. In principle the same reflected rays will be collected by the collection optics and detected by the detector irrespective of the sample height within the working limits of the system. A change in sample height within the operational range will change the lateral position of the path of the collected rays through the collection system but will not change the rays which are selected and reach the detector, nor their arrival position at the detector.

One would most naturally focus the detector at the sample receiving location. However this causes a problem that the system becomes very sensitive to the sample height (spacing between the sample and collection optics) because different amounts of light and different rays are collected and are imaged on different parts of the detector depending on the height.

The illumination arrangement may be arranged for directing an illuminating light beam at a received sample and the optical axis of the collection optics at the entrance to the collection optics may be inclined to the beam axis of the illuminating light beam.

This can help avoid collection of any specular reflection beam and provides physical separation between the illumination beam and the input of the collection optics/the collection beam.

The collection optics may comprise an off axis paraboloid mirror for focusing light from infinity and an ellipsoid mirror dimensioned to correct for aberrations of the paraboloid mirror.

The paraboloid mirror may be arranged in the optical path in the collection optics before the ellipsoid mirror.

The paraboloid mirror may be the first optical component in the collection optics.

In an alternative system suitable lenses may be used in place of the mirrors.

The size of an entrance pupil of the collection optics may be chosen to be sufficient to accommodate a predetermined range of sample to collection optics spacings.

The diameter of the paraboloid mirror may define an entrance pupil of the collection optics.

The diameter of the paraboloid mirror may be chosen to be sufficient to accommodate a predetermined range of sample to collection optics spacings.

The collection optics may comprise an intermediate focus position and an aperture may be provided at the intermediate focus position and arranged so that its image at the detector has predetermined dimensions chosen to guard against rays outside a chosen angular range reaching the detector. The predetermined dimensions may be chosen in dependence on the dimensions of the light detecting active area of the detector. The predetermined dimensions may be chosen to be substantially the same as the dimensions of the light detecting active area.

The intermediate focus position may be disposed between the paraboloid mirror and the ellipsoid mirror.

The illumination arrangement may comprise a light source. In other cases the light source might be provided outside of the illumination arrangement. The illumination arrangement may be arranged for focusing the light source substantially at infinity.

According to a third aspect of the present invention there is provided diffuse reflectance spectroscopy apparatus for use in analysing a sample comprising:

a sample receiving location for receiving a sample for analysis;

an illumination arrangement for directing light towards a received sample;

a detector for detecting light reflected by a received sample; and collection optics for directing light reflected by a received sample towards the detector, wherein the illumination arrangement one of comprises a light source and is arranged to receive light from a light source and the illumination arrangement is arranged for focusing the light source substantially at infinity.

This will lead to the light from each point on the light source being spread across the field at the sample receiving location which in turn will improve uniformity of illumination and consistency in measurements. One might more naturally focus the light source onto the sample receiving location, but this will lead to more spatial variation in illumination as an image of the light source is formed at the sample, and hence in general more variation in illumination.

The light source may comprise an incandescent lamp. The illumination arrangement may be arranged for focusing the filament of the light source substantially at infinity.

The illumination arrangement may be arranged so that any non-uniform optical surfaces in the optical path between the light source and the sample location are spaced in the optical path from any image of a carried sample.

The illumination arrangement may comprise an interferometer including a beam splitter and may be arranged so that the image of the sample is spaced in the optical path away from the beam splitter.

The illumination arrangement may comprise an entrance paraboloid mirror for collecting light from the light source. The light source may be placed in the region of the focus of the entrance paraboloid mirror. In practice the light source may be placed just beyond the focus of the entrance paraboloid mirror.

The illumination arrangement may be arranged so that the image of the sample will be in the optical path between the entrance paraboloid mirror and the beam splitter.

The illumination arrangement may comprise a J.Stop aperture provided at a focus in the optical path to block rays with an above threshold divergence.

The illumination arrangement may comprise a relay paraboloid mirror disposed in the optical path on an opposite side of the interferometer than the light source. The J.Stop aperture may be provided at the focus of the relay paraboloid mirror.

Note that in alternatives one or more of the interferometer, entrance paraboloid mirror, J.Stop aperture, and relay paraboloid mirror as well as similar components may be provided outside of the illumination arrangement of the apparatus.

The illumination arrangement may comprise an interferometer and a half beam block which is disposed substantially at a focus in the optical path for blocking light which exits the interferometer, passes said focus, and is reflected from re-entering the interferometer.

According to a fourth aspect of the present invention there is provided diffuse reflectance spectroscopy apparatus for use in analysing a sample comprising:

a sample receiving location for receiving a sample for analysis;

an illumination arrangement for directing light towards a received sample;

a detector for detecting light reflected by a received sample; and collection optics for directing light reflected by a received sample towards the detector, wherein the illumination arrangement comprises an interferometer and a half beam block which disposed substantially at a focus in the optical path for blocking light which exits the interferometer, passes said focus, and is reflected from re-entering the interferometer.

A half beam block functions because light that is reflected will return through a focus of the system on the opposite side of the optical axis than it passed in the forward direction. Thus with an obscuration placed half way across the beam at a focus half of the light is blocked in the forward direction, and if any of the light that passes is reflected this will be blocked when travelling in the reverse direction. This is useful as it avoids light passing twice through the interferometer and reaching the detector, that is it avoids double modulated light reaching the detector.

The half beam block may be disposed in the optical path between the interferometer and the light source for blocking light that exits the interferometer back towards the light source and is reflected by the light source from re-entering the interferometer.

Alternatively, the half beam block may be disposed in the optical path on the opposite side of the interferometer than the light source.

The illumination arrangement may comprise two half beam blocks, the first of which may be disposed in the optical path between the interferometer and the light source for blocking light that exits the interferometer back towards the light source and is reflected by the light source from re-entering the interferometer and the second of which may be disposed in the optical path on the opposite side of the interferometer than the light source.

Where the half beam block is disposed in the optical path between the interferometer and the light source, the light source may be displaced transversely from the optical axis towards a side of the beam which is opposite that at which the half beam block is disposed.

The half beam block will have an edge running across the beam. The edge may be curved such that the unblocked portion of the beam is crescent shaped. At the centre of the beam the edge may be substantially at the optical axis but at positions away from the centre, the edge may be retracted from the line through the optical axis which would be described by a straight edge.

This can allow more light to enter the system whilst still blocking reflected rays. Aberrations in the system will tend to mean that reflected light from half a beam allowed through by a half beam block will occupy less than half of the initial beam field on return. Thus a full straight edged half beam block is blocking more light than necessary. Using a curved edged beam block to create a crescent shaped unblocked region increases efficiency by taking the effect of the aberrations into account. The curved edged block can be considered to compensate for field distortion.

The shape of the edge of half beam block may be chosen to ensure that substantially all rays passing the block in the forward direction will, if reflected, be blocked in the reverse direction. The shape of the block may be optimised through modelling or empirically for example.

The apparatus may further comprise a reference spectrum acquiring arrangement comprising:

at least one reference sample receiving location; and a beam switching arrangement having first and second states, the first state allowing light from the illumination arrangement to reach the sample receiving location and light reflected by a carried sample to reach the collection optics; and the second state for redirecting light from the illumination arrangement towards the reference sample receiving location instead of the sample receiving location and for directing light reflected by a received reference sample towards the collection optics allowing selective detection at the detector of light reflected by a carried sample and light reflected by a carried reference sample.

According to a fifth aspect of the present invention there is provided diffuse reflectance spectroscopy apparatus for use in analysing a sample comprising:

a sample receiving location for receiving a sample for analysis;

an illumination arrangement for directing light towards a received sample;

a detector for detecting light reflected by a received sample; and collection optics for directing light reflected by a received sample towards the detector, wherein the apparatus further comprises a reference spectrum acquiring arrangement comprising:

at least one reference sample receiving location; and a beam switching arrangement having first and second states, the first state allowing light from the illumination arrangement to reach the sample receiving location and light reflected by a carried sample to reach the collection optics; and the second state for redirecting light from the illumination arrangement towards the reference sample receiving location instead of the sample receiving location and for directing light reflected by a received reference sample towards the collection optics allowing selective detection at the detector of light reflected by a carried sample and light reflected by a carried reference sample.

This can facilitate the acquisition of a reference spectrum without the user being required to present the reference sample at the "normal" sample location. Thus for example the reference sample may be stored within the apparatus in its operative position. In turn this can encourage the user to take proper reference measurements, or allow the apparatus to take reference measurements automatically without any user involvement.

Note that in the above statements the beam switching arrangement simply allows light to reach the sample and reflected light to reach the collection in the first state. However it directs light in the second state. Thus the beam switching arrangement may in fact play no role in directing light in the first state—it may be out of the optical path. This is a preferred implementation but is not essential. In other implementations the beam switching arrangement might direct light in all states or direct light in the first state but not the second, for example. Thus more generally the beam switching arrangement may cause or allow passage of light in the desired directions in each state.

The reference spectrum acquiring arrangement may comprise a reference sample disposed at the reference sample receiving location.

The reference spectrum acquiring arrangement may comprise two reference sample receiving locations. A first may be used for holding a first reference material for use in acquiring a background spectrum. A second may be used for holding a second reference material which is different from the first reference material and is for use in acquiring an operational check spectrum.

The first reference material will generally be a highly reflective "standard" material. The spectrum of that material is likely to be relatively featureless but the amplitude will change with differences in illumination intensity for example, and differences in illumination intensity will often be wavelength dependent. Thus a background spectrum acquired using such a sample is useful for normalising spectra acquired for other samples to take into account differences in the illumination characteristics at different times, in different apparatus, and so on.

The second reference material will generally be a more featureful but stable "standard" material. A spectrum acquired using the second reference material can be compared with at least one previous spectrum acquired for the second reference material to check that the apparatus appears to be operating correctly. The spectrum acquired using the second reference material may be normalised using the respective background spectrum acquired using the first reference material.

Where there are two reference material receiving locations, preferably the beam switching arrangement has a third state:

the first state allowing light from the illumination arrangement to reach the sample receiving location and light reflected by a carried sample to reach the collection optics;

the second state for redirecting light from the illumination arrangement towards the first reference sample receiving location instead of the sample receiving location and for directing light reflected by a received reference sample at the first reference sample receiving location towards the collection optics;

the third state for redirecting light from the illumination arrangement towards the second reference sample receiving location instead of the sample receiving location and for directing light reflected by a received reference sample at the second reference sample receiving location towards the collection optics, thereby allowing selective detection at the detector of light reflected by a carried sample, light reflected by a carried reference sample at the first reference sample receiving location, and light reflected by a carried reference sample at the second reference sample receiving location.

The beam switching arrangement may comprise a roof mirror pair mounted for movement between a first position corresponding to the first state and a second position corresponding to the second state, and optionally a third position corresponding to the third state.

The roof mirror pair may be mounted for linear movement.

The beam switching arrangement may comprise a drive for driving the roof mirror pair. Thus the beam switching arrangement may comprise a drive for driving the roof mirror pair in a linear movement direction.

The use of a roof mirror pair in the beam switching arrangement can allow the optical path length between the illumination arrangement/light source and the detector to be retained constant when the beam switching arrangement is in the first state, the second state, and when present, the third state.

The beam switching arrangement may be arranged for scanning a received reference sample to allow taking of measurements over an extended area of the reference sample. The scanning may be linear scanning The beam switching arrangement may be arranged to move the roof mirror pair through a range of positions in which the roof mirror pair serves to redirect light from the illumination arrangement towards the respective reference sample receiving location instead of the sample receiving location and directs light reflected by a received reference sample at the respective reference sample receiving location towards the collection optics. In this way scanning may be achieved using the roof mirror pair.

Moreover scanning can be achieved simply and effectively using a single transport mechanism both for switching between sample measurements and reference sample measurements and for scanning reference samples. Moreover the use of the roof mirror pair ensures that the optical path length between the illumination arrangement/light source and the detector can be retained constant when in the different states and during any scanning The diffuse reflectance spectroscopy apparatus may comprise a container within which is disposed the, or both the sample receiving locations. This may be a housing of the apparatus or a separate enclosure.

The diffuse reflectance spectroscopy apparatus may comprise a memory which may store an internal reference correction spectrum which represents a difference between a spectrum acquired using the apparatus from a sample placed at the sample receiving location and from the same or an identical sample placed at the reference sample receiving location.

This can then be used in correcting the background spectrum measured using the first reference material.

According to a sixth aspect of the present invention there is provided a method of manufacturing diffuse reflectance spectroscopy apparatus as defined above.

The method may comprise the steps of:
placing a sample at the sample receiving location;
acquiring a first spectrum for the sample when at the sample receiving location;
placing the same or an identical sample at the reference sample receiving location;
acquiring a second spectrum for the sample when at the reference sample receiving location;
determining an internal reference correction spectrum from the differences between the first and second spectra for use in adjusting spectra determined from samples located at the reference sample receiving location; and
storing the internal reference correction spectrum in a memory of the diffuse reflectance spectroscopy apparatus.

The diffuse reflectance spectroscopy apparatus may comprise a spectrometer.

The diffuse reflectance spectroscopy apparatus may comprise an accessory for use with a spectrometer.

In either case the spectrometer may, for example, be an FT-IR (Fourier Transform InfraRed) spectrometer.

The diffuse reflectance spectroscopy apparatus may comprise an analysis module for analysing measurements made by the detector in order to provide compositional information concerning the sample. Alternatively an analysis module may be provided separately from the reflectance spectroscopy apparatus.

In general the features of each of the aspects of the invention defined above may be used with one another. Many practical embodiments will include a combination of these features. Further each of the optional features described above following any one of the aspects of the invention can be used as optional features of each of the other aspects of the invention, and could be rewritten with changes in wording as necessary to correspond with the respective aspect of the invention. Such features are not repeated after each aspect of the invention in the interest of brevity.

Embodiments of the present invention will now be described, by way of example only, with reference to the accompanying drawings, in which.

Figure 1:
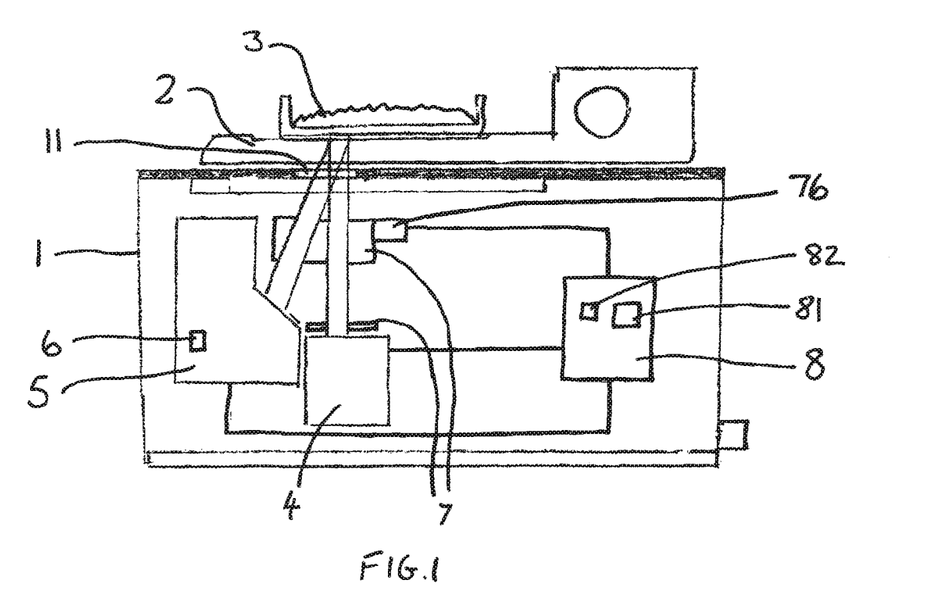
FIG. 1 schematically shows an FT-IR spectrometer embodying the present invention.

FIG. 1 schematically shows an FT-IR (Fourier Transform Infra Red) spectrometer setup for use in diffuse reflectance spectroscopy measurements. Thus the spectrometer shown in FIG. 1 constitutes diffuse reflectance spectroscopy apparatus.

The spectrometer comprises a main housing 1 disposed on top of which is a sample receiving location 2. A sample receiving location 2 may, for example, comprise a sample spinner for moving a carried sample 3 relative to the main housing 1 of the spectrometer to allow measurements to be taken over an extended area of the sample 3.

Within the housing 1 is provided an illumination arrangement 4 for directing light towards the sample 3. Further a collection system comprising collection optics 5 and a detector 6 is provided for receiving light reflected from the sample 3. The light exits the housing 1 and returns into the housing 1 via a window 11.

Also provided within the housing 1 of the spectrometer 1 is a reference spectrum acquiring arrangement 7, which will be described in more detail below, and a control unit 8 which is connected to and controls the operation of the illumination arrangement 4, the collection system 5, 6 and the reference spectrum acquiring arrangement 7. In the present embodiment the control unit 8 comprises an analysis module 81 for receiving data collected by the detector 6 and analysing this data in order to provide information concerning the composition of a measured sample 3. A memory module 82 is provided within the control unit for storing data.

Figure 2:
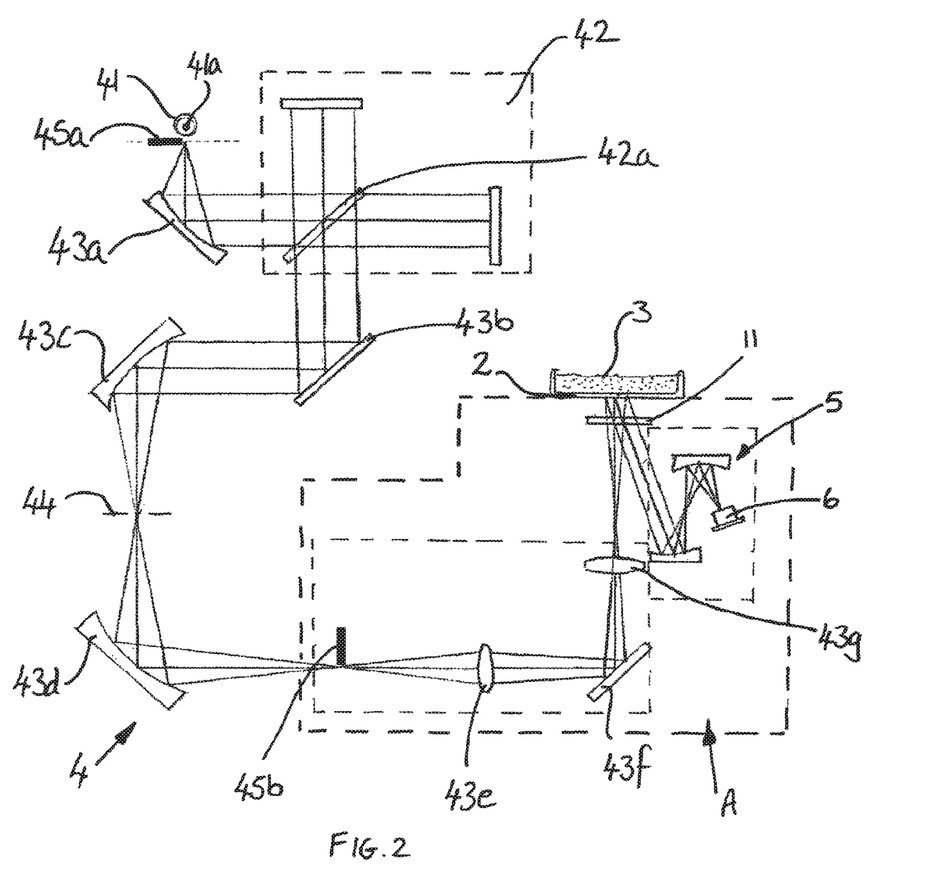
FIG. 2 schematically shows more detail of the optical arrangement of the spectrometer shown in FIG. 1.

FIG. 2 shows the optical arrangement of the spectrometer of FIG. 1 in more detail. In the present embodiment the illumination arrangement 4 comprises a light source 41, an interferometer 42 and various optical elements 43a-43g for guiding light from the source 41 to the interferometer 42 and from the interferometer 42 towards the sample receiving location 2. The illumination arrangement 4, and in particular the optical elements 43a-43g, are arranged to focus the light source 41 substantially at infinity. This leads to light from each point on the light source 41 being spread across the field at the sample receiving location 2 which in turn will improve uniformity of illumination and consistency in measurement. One might more naturally focus the light source 41 onto the sample receiving location 2. However this will lead to more spatial variation in illumination as an image of the light source 41 would then be formed at the sample.

In the present embodiment the light source 41 comprises an incandescent lamp having a filament 41a. The illumination arrangement 4 is arranged for focusing the filament 41a substantially at infinity. This is helpful because the spectral content of the light emitted by the lamp 41 will be dependent on the temperature of the filament according to Planck's law of blackbody radiation. Generally speaking, the temperature of the filament will not be constant along its length due to its shape and/or variation in thicknesses.

Generally speaking, one can expect the lamp's emission to be approximately equal in all directions and thus, by focusing the lamp at infinity, it can be expected that light from each point of the source will be spread evenly across the field at the sample location 2.

In the present embodiment the optical elements in the illumination arrangement 4 include:

an off axis paraboloid mirror 43a provided for collecting light from the source 41 and directing this towards the interferometer 42. Further there is provided a flat mirror 43b for reflecting light exiting the interferometer 42 towards a second off axis paraboloid mirror 43c, which feeds light towards an off axis ellipsoid mirror 43d, which in turn reflects the light towards a first lens 43e and onwards to a second flat mirror 43f, which reflects the light through a second lens 43g, after which light passes through the window 11 provided in the housing 1 of the spectrometer to the sample receiving location 2.

In the present embodiment the source 41 is placed a small distance beyond the focus of the first paraboloid mirror 43a and thus the rays enter the interferometer 42 converging slightly.

The interferometer 42 is used in the present apparatus to modulate the illumination beam in order to encode the spectroscopic content of the light in the conventional way for carrying out FT-IR measurements. Thus no further description of its operation is given here.

Any divergent rays within the interferometer 42 have a different path length than paraxial rays and thus will generate slightly frequency shifted modulation. This will tend to detract from the spectral resolution of the system and needs to be controlled. Thus a J.stop aperture 44 is provided at the focus of the second paraboloid mirror 43c to block highly divergent rays. The first ellipsoid mirror 43d forms an image of the J.stop aperture 44 at a focus between the ellipsoid mirror 43d and the first lens 43e. This provides a beam waist. The first and second lenses 43e and 43g and the second flat mirror 43f are used to relay the beam to a convenient sampling location whilst controlling its geometry and ensuring that an image of the source is substantially at infinity.

The second paraboloid mirror 43c and first ellipsoid mirror 43d may be chosen to be complimentary so as to minimise aberrations. In particular the first ellipsoid mirror 43d may be chosen to correct for aberrations in the second paraboloid mirror 43c.

The lenses 43e and 43g of the illumination arrangement and the path lengths are selected to give the system the following attributes:

1. A suitable beam diameter at the sample receiving location 2

2. A beam diameter which is roughly constant for a distance above and below the nominal sample location 2.

3. Minimised divergence of the beam above and below the sample location 2. This is useful as it enables the collection system axis to be less inclined relative to the illumination axis which in turn improves the system immunity to mispositioning of the sample 3.

It should be noted that whilst the main functionally important elements of the illumination arrangement 4 are shown and described with reference to FIG. 2, in a practical system they may well be further optical elements in the path performing conventional functions.

As a whole there may be a relatively large number of optical elements in the path between the source 41 and the sample location 2. In order to promote uniformity of illumination at the sample, the optical elements 43a to 43f as well as components within the interferometer 42 are arranged so that any surface which may be non-uniform is spaced from an image (conjugate) of the sample. As an example, in the interferometer 42 there is a beam splitter 42a which can have a response that varies significantly over its surface. Thus the optical system in the present embodiment is arranged so that the conjugate of the sample is at a reasonable distance from the beam splitter 42a. In the present embodiment the conjugate of the sample lies in the optical path between the beam splitter 42a and the first paraboloid mirror 43a.

A possible problem when using FT-IR spectroscopy is that of the presence of a double modulation artefact in measured spectra. Such an artefact creates a false indication of short wavelength/high frequency energy in the spectrum. The presence of such false energy in the spectrum has the potential to influence chemometric predictions and therefore differences in the magnitude of any such artefact between instruments can adversely affect the effectiveness of the calibration and the possibility of reusing calibrations across different instruments.

Double modulation artefact is caused by light passing twice through the interferometer 42. If light is allowed to pass twice through the interferometer 42 it will be modulated on each pass and this will lead to unwanted and erroneous responses at the detector 6 if this light passes through the whole of the system. Thus in the present embodiment two half beam blocks are used in an effort to suppress any double modulation artefact.

As mentioned above the double modulation artefact comes about if light is allowed to pass through the interferometer 42 twice. Generally speaking this can occur because when light enters the interferometer 42, half of the light will be reflected back out of the interferometer 42 in the input direction, whilst half of the light travels forwards. This means that there are reflective components before or after the interferometer 42 there is an opportunity for the light to re-enter the interferometer 42 and then re-emerge again.

One possibility to try to reduce the strength of double modulation artefact is to reduce the back reflection of all component parts in the optical path or to otherwise try to redirect or block doubly modulated light from reaching the detector. This can be difficult. On the other hand, the use of half beam blocks provides a particularly convenient way to avoid light passing through the interferometer 42 twice and hence stop (or at least significantly reduce) receipt of double modulated light at the detector 6.

A half beam block consists of an obscuration placed across half of the beam at a focus. Such a half beam block effectively stops (or at least significantly reduces) the generation of double modulated light because when light passes the focus in one half of the beam and is then reflected back towards the beam block it will return on the opposite side of the optical axis than it was when it passed the focus in the forward direction. Thus the half of the beam which can pass the beam block in the forward direction will impact on the beam block when travelling back in the reverse direction if it is reflected. Of course on the other hand, the portion of the beam which meets the beam block in the forward direction proceeds no further.

In the present embodiment a first half beam block 45a is provided at a focus of the first paraboloid mirror 43a just in front of the light source 41 and a second half beam block 45b is provided at a focus of the first ellipsoid mirror 43d. The first half beam block 45a serves to block any light which exits the interferometer 42 in the reverse direction back towards the light source 41 from being reflected at the light source 41 and progressing back towards the interferometer 42.

On the other hand, the second half beam block 45b blocks the return to the interferometer 42 of any light reflected by, say, lenses 43e or 43g, the window 11 or the sample 3 or sample holder.

Each half beam block 45a, 45b is blackened to ensure that as far as possible it does not reflect light.

Figure 4A:
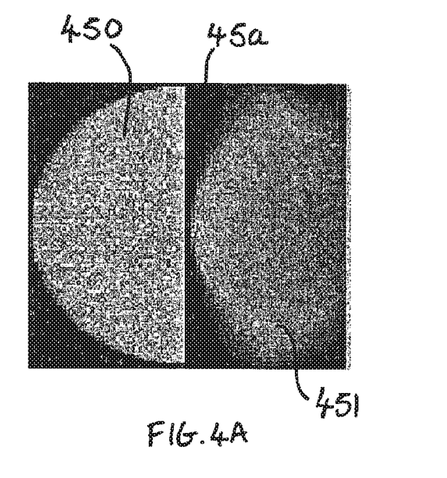
FIG. 4A illustrates a straight edge half beam block which may be used in the spectrometer shown in FIGS. 1 and 2 as well as its effect on light passing through the system.

A straight edged half beam block 45a, 45b, positioned halfway across the beam or just over half way across the beam, will act to significantly reduce or remove any double modulation artefact by effectively blocking the return of light which passes the half beam block. However due to aberrations in the system, light which passes the half beam block and is returned may actually occupy a field which is smaller than half the beam. FIG. 4A illustrates this effect.

FIG. 4A shows (in the right hand half of the Figure) a straight edged half beam block which might for example be used as the first half beam block 45a. This is blackened and has a straight edge which can be seen down the centre of the image shown in FIG. 4A. This half beam block, blocks half of the beam such that half of the beam 450 may pass the beam block in the forward direction. If this light is reflected and returns back towards the half beam block then, due to aberrations in the system, the shape of the beam will have changed. An example of what a returned half beam looks like after reflection can be seen on the right hand half of FIG. 4A and is labelled 451. Thus it will be seen that whilst near the centre of the beam the returned beam is still close to the edge of the half beam block at regions away from this centre the edge of the beam has retracted. Thus the dark area of the half beam block 45a shown between the two beam portions 450 and 451 is not in fact performing a useful function. This part of the beam block 45a is not needed to block the return beam. Thus it is possible to use a modified shape of half beam block in order to increase the amount of the beam which is allowed to pass the half beam block. This means that illumination efficiency can be increased.

Figure 4B:
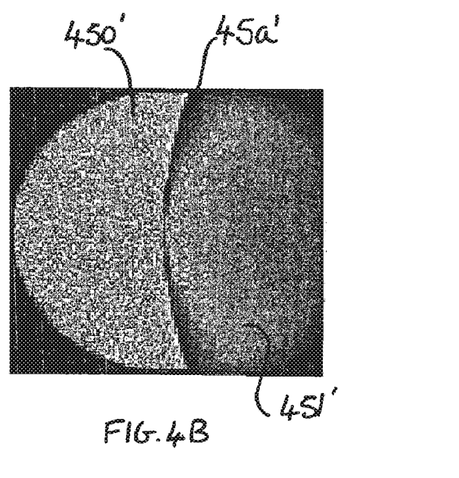
FIG. 4B shows a curved edged half beam block which may be used in the spectrometer of FIGS. 1 and 2 as well as its effect on light passing through the system.

In FIG. 4B a curved edge half beam block 45a' is illustrated. This half beam block could be used in the same way as the straight edged half beam block 45a, or indeed the second half beam block 45b. Here, by taking into account the aberrations which occur in the system, the shape of the half beam block 45a' is chosen so that the beam 450' which is allowed to pass the half beam block has a crescent shape. Again when the beam is reflected and returned its shape is changed by aberration. This is illustrated by the lighter region 451' shown in the image of FIG. 4B. There is still a dark region between the forward beam 450' and reflected beam 451'. Thus the half beam block 45a' is still functioning to block reflected light and hence will prevent or at least significantly reduce any double modulation artefact but on the other hand, the amount of light initially let through by the half beam block 45a' is significantly increased.

Figure 5A:
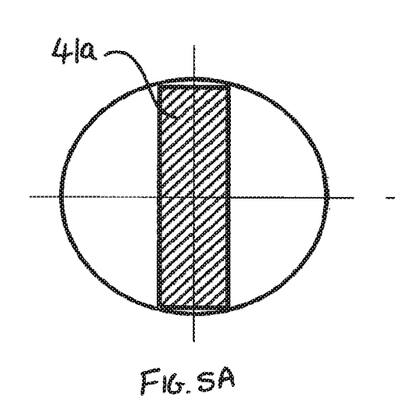
FIG. 5A schematically shows how a filament of a light source may be positioned relative to the acceptance field of an illumination arrangement of the spectrometer shown in FIG. 1 and FIG. 2.
Figure 5B:
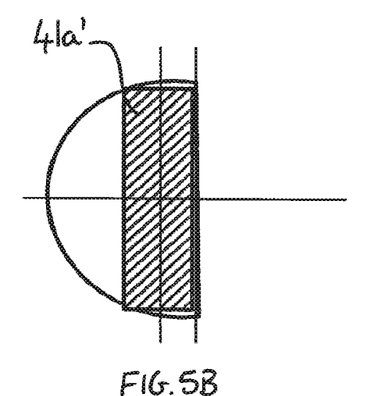
FIG. 5B shows a filament of a light source which is offset with respect to the acceptance field.

Another technique may be used to further increase the efficiency of the system where a first half beam block 45a is used in the region of the source 41. This is to arrange the source 41 so that the filament 41a is offset with regard to the optical axis. FIG. 5A shows the filament 41A aligned with the optical axis in a way which will allow the system to function. However in FIG. 5B the filament is shown to be offset in the direction of the open half of the beam i.e. away from the side blocked by the half beam block 45a. This means that more light from the filament is allowed to enter the system rather than being directly blocked by the half beam block 45a.

Following the above description of the illumination arrangement 4, now more consideration is given to the collection system 5, 6.

Diffusely reflecting samples emit rays of light over a wide range of angles. A traditional approach in diffuse reflectance spectroscopy is to collect light over as much of this angular range as possible. This might involve using an integrating sphere to collect the light. A particular problem with such a system is that the change in the distance between the sample and the entrance into the integrating sphere can produce significant changes in measured spectra due to the angle of rays which will be collected and/or the intensity of light which will be collected. Furthermore in practice integrating spheres tend to be inhomogeneous in themselves and there tend to be differences between one sphere and the next. Thus this traditional type of arrangement is unsatisfactory where the aim is to provide a system which is tolerant to different conditions and where different versions of the instrument are to behave as similarly as possible.

As mentioned above, the illumination arrangement 4 is designed to have a beam diameter that is roughly constant for a distance above and below a nominal sample location associated with the sample receiving location 2 and also to minimise the divergence of the beam above and below the sample location. This helps towards the apparatus being insensitive to the positioning or height of the sample 3 in relation to the apparatus. The collection optics 5 are similarly arranged with a view to provide insensitivity to the height of the sample 3 in relation to the system.

This is important because, as illustrated for example in FIGS. 1 and 2, the sample 3 is likely to be provided at the sample receiving location 2 in some kind of container such as a petri dish or sample bottle. The lower wall of such a container through which the interrogating radiation must pass to reach the sample 3 will tend to vary from container to container. Thus the height of the sample 3 is likely to vary to some degree.

Figure 3:
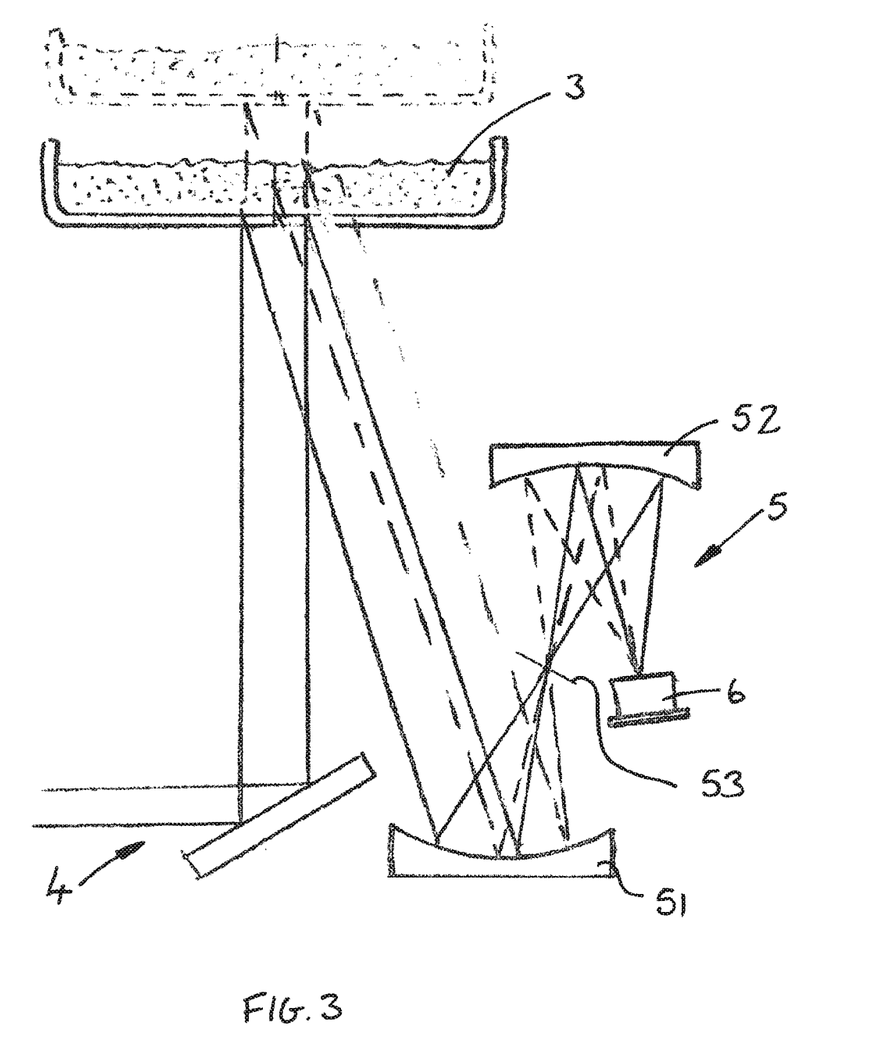
FIG. 3 schematically shows the effect of changing the sample height of the operation of collection optics of the spectrometer shown in FIGS. 1 and 2.

FIG. 3 shows the collection optics 5 on a larger scale and also illustrates the effect of changing the sample height in the present system. Note that in FIG. 3 only a simplified version of the illumination arrangement 4 is shown. The collection optics 5 comprise a collection off axis paraboloid mirror 51 and a second ellipsoid mirror 52 which is chosen in order to correct aberrations in the paraboloid 51. Note however in an alternative configuration lenses might be used in place of the mirrors 51, 52.

The collection optics 51, 52 are arranged to collect light reflected from the sample 3 at the sample receiving location 2 over a small and well defined range of angles and the collection optics 51, 52 are chosen so that the detector 6 is effectively focused at infinity. Further the collection optics 5 and detector 6 are positioned so that the collection system axis is inclined from the illumination beam direction, in this case from the vertical. This helps avoid collection of any specular reflection from the window 11 of the housing 1 and/or any sample container. It also means that the reflected beam is separated from the illumination beam.

Because the detector 6 is focused at infinity, the active area of the detector will limit the angular range of rays emitted by the sample which will be detected. This angular range will be small, typically in the region of a few degrees.

The diameter of the collection parabaloid mirror 51 defines the entrance pupil of the system. It is selected to be sufficiently large to accommodate all rays from the illuminated region of the sample 3 which are emitted within the design angular acceptance range.

If the sample is displaced vertically, as illustrated by dotted lines in FIG. 3, this causes lateral displacement of the collection beam in the collection optics 5. However, as the detector 6 is focused at infinity, such a displacement does not cause any change in the angular range of the rays collected. Since the entrance pupil is large enough to accommodate this displacement (assuming that the vertical displacement is not beyond the operational range of the system), all of the rays within the design angular range are still routed to the detector 6. Moving the sample 3 has changed the routing of rays within the collection optics 5 but has not changed the rays which are selected and directed to the detector 6. Furthermore, since the mirrors are very uniform reflectors, this change of routing of the rays should have little or no effect on the intensity or spectrum of the light incident on the detector 6. Further, because the detector 6 is focused on infinity, the rays from the sample reaching the detector will reach the same area of the detector irrespective of the height of the sample (within operational range).

All of these factors help to provide uniformity in the performance of the system and between one instrument and another.

Thus within the working range of the system, the measured spectrum of a sample should be independent of the sample height.

Note that in a typical system it would be normal to focus the detector at the sample location but it has been realised by the present applicants that focusing the detector at infinity leads to the above-mentioned advantages.

An intermediate focus position is available between the two mirrors 51 and 52 and an aperture 53 is placed at this focus to guard against rays outside the chosen angular range region reaching the detector 6. The aperture 53 may be chosen so that the image of the aperture 53 at the detector 6 is the same as, or slightly larger than the active area of the detector 6.

It should be noted that the sample 3 will emit light over a very broad range of angles, although the collection optics 5 are designed to accept only reflections over a relatively narrow and predetermined range of angles. Without the aperture 53, highly divergent light from the sample 3 might strike the housing of the detector. Some of such rays might reflect off the housing and strike the active area.

Figure 6:
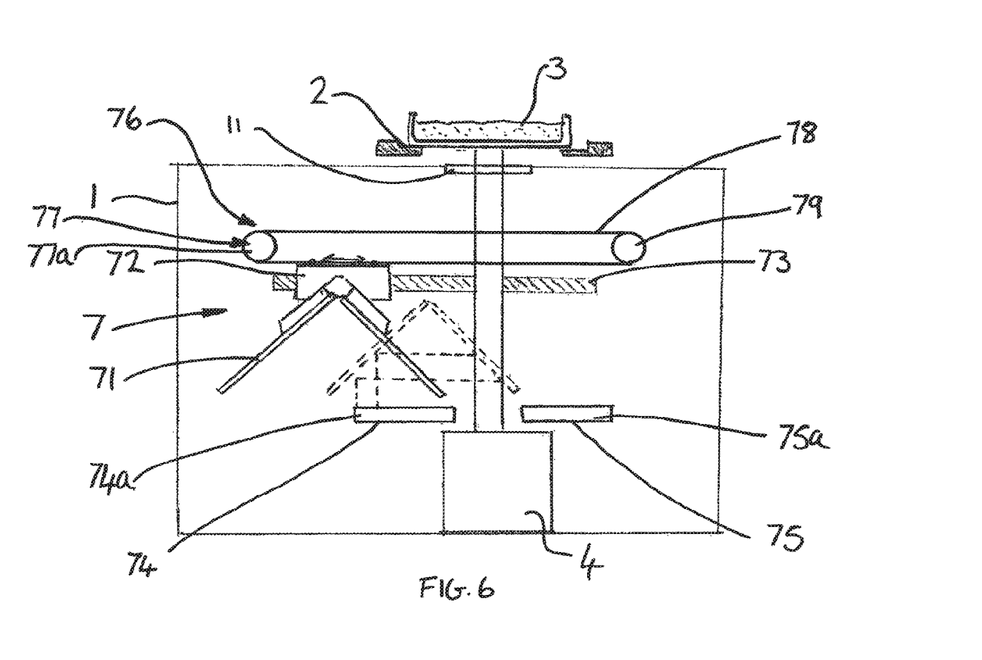
FIG. 6 schematically shows part of the spectrometer shown in FIGS. 1 and 2 including a reference spectrum acquiring arrangement of the spectrometer.

FIG. 6 shows part of the spectrometer of FIG. 1 from a direction which is at right angles to the direction shown in FIG. 1. In the view shown in FIG. 6, the illumination arrangement 4, the sample receiving location 2, the window 11 in the housing 1, and the reference spectrum acquiring arrangement 7 can be seen, however the collection system 5, 6 and control unit 8 cannot be seen. The plane of illumination and collection beams is perpendicular to the plane of the paper with the device orientated as shown in FIG. 6.

FIG. 6 shows the reference spectrum acquiring arrangement 7 in more detail than FIG. 1. The reference spectrum acquiring arrangement comprises a roof mirror pair 71 mounted via a linear bearing 72 on a linear guide 73 and comprises a drive arrangement 76 for driving the roof mirror pair 71 relative to the linear guide 73 and hence relative to the illumination arrangement 4 as well as the collection system 5, 6. The drive arrangement 76 comprises a motor 77 with a respective pulley 77*a* and a toothed belt 78 mounted on the motor pulley 77*a* and an idler pulley 79. The toothed belt 78 is attached to the linear bearing 72 to transfer drive to the roof mirror pair 71.

The reference spectrum acquiring arrangement 7 also comprises a first reference sample receiving location 74 and a second reference sample receiving location 75. The reference sample receiving locations 74, 75 are provided on opposing sides of the plane of the illumination and collection beams. In the present embodiment a first reference sample 74*a* is provided at the first reference receiving location 74 and a second reference material 75*a* is provided at the second reference material location 75. In the present embodiment the first reference material 74*a* is a highly reflective and generally featureless standard material such as spectralon (a sintered PTFE material), or gold deposited on a scattering surface—"diffuse gold" whereas the second reference material 75*a* is another standard material which is stable but which has rather more features in its infrared spectrum. Such a material might, for example, be PVC, or a tablet made from a mixture of rare earth oxides.

The roof mirror pair 71 is mounted for linear movement in a direction which is perpendicular to the plane of the illumination and collection beams. The mirrors in the roof mirror pair 71 are set at right angles to one another. An apex where the mirrors meet or would meet is arranged at right angles to their linear movement direction. The mirrors project downwardly from this apex towards the first and second sample receiving locations 74, 75.

The roof mirror pair 71 and its transport mechanism 72, 73 together act as a beam switching arrangement which is useable for selectively allowing measurement of spectra of samples carried at the sample receiving location 2 on the one hand and an acquiring spectra from the first reference material 74a and/or second reference material 75a on the other hand.

When the roof mirror pair 71 is in the location shown on solid lines in FIG. 6 it is displaced from the optical axis through the apparatus such that it has no effect on the delivery of light by the illumination arrangement 4 and the collection of light by the collection system 5, 6. Thus with the roof mirror pair 71 in the position shown in FIG. 6, the spectrometer is able to operate as described above with the illumination beam leaving the illumination arrangement 4, progressing to the sample receiving location 2 and impinging on any provided sample 3, before being reflected by the sample 3 towards the collection system 5, 6.

However if the roof mirror pair 71 is moved along its linear guide 73 to the position shown in dotted lines in FIG. 6, the roof mirror pair 71 interrupts this path for light through the system. In particular, as shown again in dotted lines in FIG. 6, the illumination beam from the illumination arrangement 4 will be reflected via the roof mirror pair 71 onto the first reference sample 74a. Further, although not depicted in FIG. 6, light reflected by the first reference sample 74a (at the appropriate acceptance angles) will be reflected by the roof mirror pair 71 back towards the collection optics 5. Light is reflected first by one of the mirrors in the pair and then by the respective other mirror in the pair as it is reflected by the roof mirror pair in each direction.

The beam switching arrangement made up of the roof mirror pair 71 and its transport arrangement 72, 73 may be considered to have different states.

In a first state, as shown in solid lines in FIG. 6, the beam switching arrangement allows the detector 6 of the collection arrangement to collect light reflected from the sample 3 located at the "normal" sample receiving location. However, the beam switching arrangement has other states which allow the detector 6 to detect light reflected from the first reference sample 74a or the second reference sample 75a as is described in more detail below with reference to FIGS. 7A, 7B and FIG. 8.

Furthermore, the roof mirror 71 and its transport arrangement 72, 73 may be used for scanning the reference sample 74a and/or 75a to provide spatial averaging when spectra are taken from these reference samples.

Figure 7A:
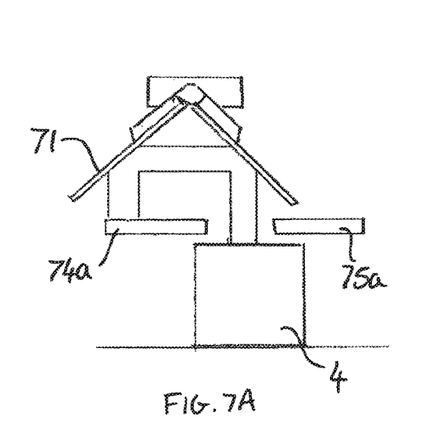
FIG. 7A schematically shows a roof mirror of the reference spectrum acquiring arrangement shown in FIG. 6 in a first position in relation to a first reference sample to facilitate acquiring of a reference spectrum in respect of the first reference sample.
Figure 7B:
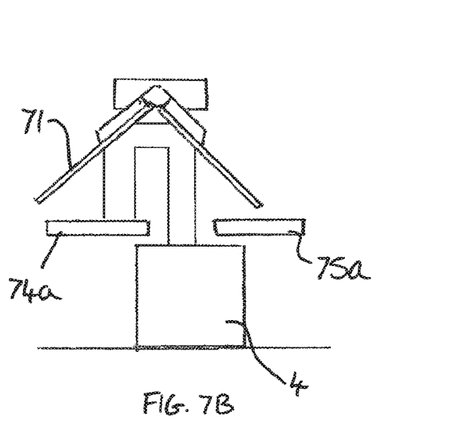
FIG. 7B shows the roof mirror shown in FIG. 7A in a second position with respect to the first reference sample.
Figure 8:
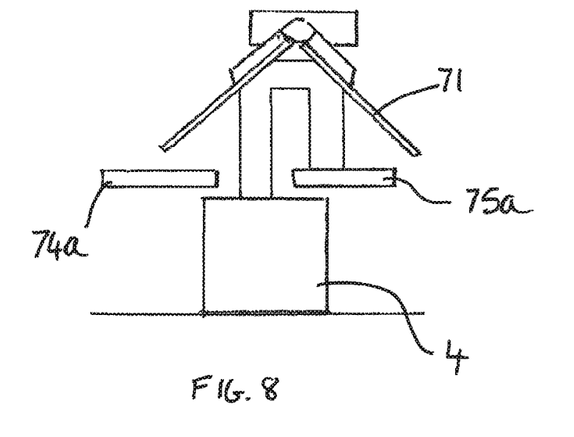
FIG. 8 shows the roof mirror as shown in FIGS. 6, 7A and 7B in a position where it facilitates acquiring a reference spectrum in respect of a second reference material.

As illustrated in FIG. 7A, with the roof mirror pair 71 in a particular location, light may be fed to and reflected back from a first location on the first reference material sample 74a. As the roof mirror pair 71 is moved in a linear direction (which is to the right in the orientation shown in FIGS. 7A and 7B) light will be fed to and reflected from a different portion of the first reference material 74a. Thus by moving the roof mirror pair 71 through a series of positions between those shown in 7A and 7B the illumination beam may be linearly scanned across the first reference material 74a such that an area of this reference material 74a can be irradiated and light reflected therefrom can be collected for analysis. Similarly, by moving the roof mirror pair 71 further in the same direction (i.e. towards the right in the orientation shown in FIGS. 7A, 7B and 8) the roof mirror pair 71 may be brought to another position, as shown in FIG. 8, where light from the illumination arrangement 4 is fed to the second reference material sample 75a and the apparatus may be used for collecting spectra therefrom. Further it will be appreciated that the roof mirror pair 71 may be moved in such a way as to scan the illumination beam and collection area across the second reference material sample 75a.

Thus the provision of the roof mirror pair 71 and a single linear transport mechanism 72, 73 allows three way beam switching such that the same illumination arrangement 4 and collection system 5, 6 may be used with the main sample receiving location 2 as well as two different reference sample receiving locations 74 and 75. Furthermore this is achieved using only a single transport mechanism.

Further, the apparatus may be arranged so that the path length through the system, when light is being fed to and reflected from a sample at the main sample receiving location 2, is the same as the path length when light is being fed to and reflected from a sample at the first reference sample receiving location 74 and the second reference sample receiving location 75. Furthermore this path length may be maintained the same as the beam is scanned across the first reference sample material 74a and/or second reference sample material 75a. This equality of the path length during switching and the scanning operations is facilitated by using the roof mirror pair 71. This may be appreciated from considering, for example, FIGS. 7A, 7B and 8. It can be noted, for example, when comparing the optical paths in FIGS. 7A and 7B, that in FIG. 7A there is a greater horizontal component of the optical path whereas in FIG. 7B there is a greater vertical component in the optical path (in the orientation shown in FIGS. 7A and 7B).

The first and second reference material 74a and 75a may be retained within an enclosure in the spectrometer. This may, for example, be the main housing 1 of the spectrometer.

This means that the reference sample materials 74a, 75a may be retained in their operative positions ensuring that they are protected and removing the need for the user to present reference sample materials at the main sample receiving location 2. This means that reference measurements are more likely to be taken and/or can be taken automatically by the apparatus without intervention of the user.

The first reference sample material 74a may be used to take a background spectrum measurement from time to time to allow compensation for changes in illumination which may occur from time to time due to, for example, changes in the output of the light source.

Such a background spectrum may be used for normalising other spectra taken of samples 3 presented at the main sample receiving location 2.

On the other hand the second reference sample 75a may be used to enable an operational check to be made in respect of the spectrometer.

During manufacture, or at first use, a spectrum for the second reference material 75a may be taken and stored in the memory module 82 in the control unit 8. At a later time another spectrum for the same second reference material 75a may be taken and compared with that stored in the memory module 82. If the later taken spectrum differs from the stored one by more than a threshold amount, this can be taken as an indication that the device has ceased to function properly. The device may be arranged to issue an alert if this condition is determined.

The memory module 82 may also store an internal reference correction spectrum. This correction spectrum may be determined during manufacture and is representative of differences which will occur in the spectrum when a sample is interrogated when in position at one of the reference sample locations 74, 75 rather than at the main sample receiving location 2. This correction spectrum can be obtained during manufacture by presenting a sample at the main sample receiving location 2 and obtaining a spectrum and then obtaining a spectrum for the same sample (or an identical sample) positioned at one of the reference sample receiving locations. From these two spectra the internal reference correction spectrum may be determined. This internal reference correction spectrum may then be used to further hone the background spectrum which is acquired from the first reference sample material 74a for use in correcting spectra obtained from "target" samples placed at the main sample receiving location 2. The internal reference correction spectrum allows the background spectrum to be adjusted to be closer to what would have been measured if the first reference sample material was placed at the main sample receiving location 2.

Note that in alternatives rather than the diffuse reflectance apparatus being a complete spectrometer including everything from the light source to the analysis module, the diffuse reflectance apparatus may comprise some subset of the parts. Thus, for example, the apparatus may be an accessory or kit for use with an existing spectrometer. Typically an accessory might comprise only part of the optics shown in FIG. 2. A dotted line box labelled A in FIG. 2 shows what an accessory may comprise. Thus the accessory A may include only part of the illumination arrangement 4 of the spectrometer described above. Although that part can still be considered "an illumination arrangement". The accessory A in this case also includes the sample receiving location 2, the collection system 5, 6 and the reference spectrum acquiring arrangement 7 (although this is not shown in FIG. 2). Notably the light source 41 and interferometer 42 are not included in this example accessory A and nor is the analysis module 81. These parts will be in the existing/separate spectrometer for use with the accessory A. The accessory A may be provided as part of a kit including a beam block 45a to mount near the source 41 and/or software to load into the spectrometer or its controlling computer.

The invention claimed is:

1. Diffuse reflectance spectroscopy apparatus for use in analysing a sample comprising:
   a light source;
   a sample receiving location for receiving a sample for analysis;
   an illumination arrangement for directing light from the light source towards a received sample;
   a detector for detecting light reflected by the received sample; and
   collection optics for directing light reflected by the received sample towards the detector, wherein the illumination arrangement comprises an interferometer and a half beam block disposed substantially at a focus in the optical path between the interferometer and the light source for blocking light that exits the interferometer back towards the light source and is reflected by the light source from re-entering the interferometer,
   wherein the light source is displaced transversely from the optical axis towards a side of the beam which is opposite that at which the respective half beam block is disposed.

2. Diffuse reflectance spectroscopy apparatus according to claim 1 in which the illumination arrangement comprises a second half beam block, which is disposed in the optical path on the opposite side of the interferometer than the light source.

3. Diffuse reflectance spectroscopy apparatus according to claim 1 in which the half beam block has an edge running across the beam and the edge is curved such that the unblocked portion of the beam is crescent shaped.

4. Diffuse reflectance spectroscopy apparatus according to claim 3 in which the shape of the edge of half beam block is chosen to ensure that substantially all rays passing the block in the forward direction will, if reflected, be blocked in the reverse direction.

5. Diffuse reflectance spectroscopy apparatus according to claim 1 in which the illumination arrangement is arranged for focusing the light source substantially at infinity.

6. Diffuse reflectance spectroscopy apparatus according to claim 5 in which the light source comprises an incandescent lamp and the illumination arrangement is arranged for focusing the filament of the light source substantially at infinity.

7. Diffuse reflectance spectroscopy apparatus according to claim 5 in which the illumination arrangement is arranged so that any non-uniform optical surfaces in the optical path between the light source and the sample location are spaced in the optical path from any image of a carried sample.

8. Diffuse reflectance spectroscopy apparatus according to claim 7 in which the illumination arrangement comprises an interferometer including a beam splitter and is arranged so that the image of the sample is spaced in the optical path away from the beam splitter.

9. Diffuse reflectance spectroscopy apparatus according to claim 5 in which the illumination arrangement comprises an entrance paraboloid mirror for collecting light from the light source, and the light source is placed beyond a focus of the entrance paraboloid mirror.

10. Diffuse reflectance spectroscopy apparatus according to claim 1 wherein the collection optics is arranged for directing towards the detector, light reflected at an angle within a predetermined angular range by a received sample, wherein the collection optics focus the detector substantially at infinity.

11. Diffuse reflectance spectroscopy apparatus according to claim 10 in which the illumination arrangement is arranged for directing an illuminating light beam at a received sample and the optical axis of the collection optics at the entrance to the collection optics is inclined to the beam axis of the illuminating light beam.

12. Diffuse reflectance spectroscopy apparatus according to claim 10 in which the size of an entrance pupil of the collection optics is chosen to be sufficient to accommodate a predetermined range of sample to collection optics spacings.

13. Diffuse reflectance spectroscopy apparatus according to claim 10 in which the collection optics comprises an intermediate focus position and an aperture is provided at the intermediate focus position and arranged so that its image at the detector has predetermined dimensions chosen to guard against rays outside a chosen angular range reaching the detector, the predetermined dimensions may be chosen in dependence on the dimensions of the light detecting active area of the detector.

14. Diffuse reflectance spectroscopy apparatus according to claim 10 in which the collection optics comprise an off axis paraboloid mirror for focusing light from infinity and an ellipsoid mirror dimensioned to correct for aberrations of the paraboloid mirror.

15. Diffuse reflectance spectroscopy apparatus according to claim 1 which further comprises a reference spectrum acquiring arrangement comprising:
  at least one reference sample receiving location; and
  a beam switching arrangement having first and second states,
    the first state for causing or allowing light from the illumination arrangement to reach the sample receiving location and light reflected by a carried sample to reach the collection optics; and
    the second state for causing or allowing light from the illumination arrangement to reach the reference sample receiving location instead of the sample receiving location and causing or allowing light reflected by a received reference sample to reach the collection optics allowing selective detection at the detector of light reflected by a carried sample and light reflected by a carried reference sample.

16. Diffuse reflectance spectroscopy apparatus according to claim 15 in which the reference spectrum acquiring arrangement comprises a reference sample disposed at the reference sample receiving location.

17. Diffuse reflectance spectroscopy apparatus according to claim 15 in which the reference spectrum acquiring arrangement comprise two reference sample receiving locations.

18. Diffuse reflectance spectroscopy apparatus according to claim 17 in which a first of the reference sample receiving locations holds a first reference material for use in acquiring background spectrum and a second of the reference sample receiving locations holds a second reference material which is different from the first reference material and is for use in acquiring an operational check spectrum.

19. Diffuse reflectance spectroscopy apparatus according to claim 17 which is arranged to acquire a background spectrum from a reference sample held at the first reference sample receiving location and acquire an operational check spectrum from a reference sample held at the second reference sample receiving location.

20. Diffuse reflectance spectroscopy apparatus according to claim 17 in which the beam switching arrangement has a third state:
  the first state for causing or allowing light from the illumination arrangement to reach the sample receiving location and light reflected by a carried sample to reach the collection optics;
  the second state for causing or allowing light from the illumination arrangement to reach the first reference sample receiving location instead of the sample receiving location and for causing or allowing light reflected by a received reference sample at the first reference sample receiving location to reach the collection optics;
  the third state for causing or allowing light from the illumination arrangement to reach the second reference sample receiving location instead of the sample receiving location and causing or allowing light reflected by a received reference sample at the second reference sample receiving location to reach the collection optics,
  thereby allowing selective detection at the detector of light reflected by a carried sample, light reflected by a carried reference sample at the first reference sample receiving location, and light reflected by a carried reference sample at the second reference sample receiving location.

21. Diffuse reflectance spectroscopy apparatus according to claim 15 in which the beam switching arrangement comprises a roof mirror pair mounted for movement between a first position corresponding to the first state and a second position corresponding to the second state.

22. Diffuse reflectance spectroscopy apparatus according to claim 21 in which the roof mirror pair is mounted for linear movement.

23. Diffuse reflectance spectroscopy apparatus according to claim 21 in which the beam switching arrangement comprises a drive for driving the roof mirror pair.

24. Diffuse reflectance spectroscopy apparatus according to claim 21 in which the use of the roof mirror pair in the beam switching arrangement allows the optical path length between the illumination arrangement/light source and the detector to be retained constant when the beam switching arrangement is in the first state, and the second state.

25. Diffuse reflectance spectroscopy apparatus according to claim 15 in which the beam switching arrangement is arranged for scanning a received reference sample to allow taking of measurements over an extended area of the reference sample.

26. Diffuse reflectance spectroscopy apparatus according to claim 24 in which the beam switching arrangement is arranged for scanning a received reference sample to allow taking of measurements over an extended area of the reference sample and the use of the roof mirror pair in the beam switching arrangement allows the optical path length between the illumination arrangement/light source and the detector to be retained constant when the beam switching arrangement is used in scanning.

27. Diffuse reflectance spectroscopy apparatus according to claim 15 in which the diffuse reflectance spectroscopy apparatus comprises a memory storing an internal reference correction spectrum which represents a difference between a spectrum acquired using the apparatus from a sample placed at the sample receiving location and from the same or an identical sample placed at the reference sample receiving location.

28. A method of manufacturing diffuse reflectance spectroscopy apparatus according to claim 15, the method comprising the steps of:
  placing a sample at the sample receiving location;
  acquiring a first spectrum for the sample when at the sample receiving location;
  placing the same or an identical sample at the reference sample receiving location;
  acquiring a second spectrum for the sample when at the reference sample receiving location;
  determining an internal reference correction spectrum from the differences between the first and second spectra for use in adjusting spectra determined from samples located at the reference sample receiving location; and
storing the internal reference correction spectrum in a memory of the diffuse reflectance spectroscopy apparatus.

29. Diffuse reflectance spectroscopy apparatus according to claim 1 in which the half beam block has an edge running across the beam and the edge is curved such that a cross-section of the unblocked portion of the beam taken perpendicularly to the beam axis is crescent shaped.

30. Diffuse reflectance spectroscopy apparatus for use in analysing a sample comprising:
  a sample receiving location for receiving a sample for analysis;
  an illumination arrangement including
    a light source;
    an interferometer; and
    a half beam block disposed substantially at a focus in the optical path between the interferometer and the light source, the half beam block being configured to allow light to pass from the light source to the interferometer, and the half beam block being configured to block light that exits the interferometer back towards the light source and is reflected by the light source from re-entering the interferometer;

a detector for detecting light reflected by a received sample; and collection optics for directing light reflected by the received sample towards the detector, wherein the light source is displaced transversely from the optical axis towards a side of the beam which is opposite that at which the respective half beam block is disposed.

31. Diffuse reflectance spectroscopy apparatus for use in analysing a sample comprising:

a light source;

a sample receiving location for receiving a sample for analysis;

an illumination arrangement for directing light from the light source towards a received sample, the illumination arrangement including an interferometer; and a half beam block disposed substantially at a focus in the optical path between the interferometer and the light source, the half beam block having a geometry that increases illumination efficiency while blocking light that exits the interferometer back towards the light source and is reflected by the light source from re-entering the interferometer;

a detector for detecting light reflected by the received sample; and collection optics for directing light reflected by the received sample towards the detector, wherein the light source is displaced transversely from the optical axis towards a side of the beam which is opposite that at which the respective half beam block is disposed.

32. Diffuse reflectance spectroscopy apparatus for use in analysing a sample comprising:

a light source;

a sample receiving location for receiving a sample for analysis;

an illumination arrangement for directing light from the light source towards a received sample, the illumination arrangement including an interferometer; and a half beam block disposed substantially at a focus in the optical path between the interferometer and the light source, the half beam block being configured to reduce or remove double modulation artefact;

a detector for detecting light reflected by the received sample; and collection optics for directing light reflected by the received sample towards the detector, wherein the light source is displaced transversely from the optical axis towards a side of the beam which is opposite that at which the respective half beam block is disposed.

* * * * *